United States Patent [19]

Brunnee et al.

[11] 4,259,572
[45] Mar. 31, 1981

[54] IONIZATION OF ORGANIC SUBSTANCES ON CONVEYOR MEANS IN MASS SPECTROMETER

[76] Inventors: Curt Brunnee, Birkenweg 24, 2820 Platjenwerbe; Jochen Franzen, Backskamp 24, 2878 Wildenhausen; Stefan Meier, Reinstrasse 68, 2800 Bremen, all of Fed. Rep. of Germany

[21] Appl. No.: 39,478

[22] Filed: May 16, 1979

Related U.S. Application Data

[63] Continuation-in-part of Ser. No. 855,579, Nov. 29, 1977, Pat. No. 4,178,507.

[30] Foreign Application Priority Data

Nov. 29, 1976 [DE] Fed. Rep. of Germany ....... 2654057

[51] Int. Cl.³ ...................... H01J 27/00; B01D 59/44
[52] U.S. Cl. .................................. 250/281; 250/288; 250/423 R; 250/423 P
[58] Field of Search ................... 250/281, 288, 423 R, 250/282, 423 P; 73/61.1 C

[56] References Cited

U.S. PATENT DOCUMENTS

| | | | |
|---|---|---|---|
| 2,618,750 | 11/1952 | Parsegian et al. | 250/288 |
| 3,128,619 | 4/1964 | Lieberman | 73/61.1 C |
| 3,308,292 | 3/1967 | VonArdenne | 250/423 R |
| 3,667,917 | 6/1972 | Brandt | 73/61.1 C |
| 3,896,661 | 7/1975 | Parkhurst | 73/61.1 C |
| 4,107,537 | 8/1978 | Forsen et al. | 250/423 P |

*Primary Examiner*—Harold A. Dixon
*Attorney, Agent, or Firm*—Sughrue, Rothwell, Mion, Zinn and Macpeak

[57] ABSTRACT

Organic samples from a liquid chromatograph are deposited on a conveyor belt which transports them into a vacuum chamber at the entry end of a mass spectrometer. The samples are ionized directly on the belt by particle bombardment or by means of a laser beam. Ionization is enhanced by applying an oxide layer to the belt, by neutralizing the image force, and by vaporizing alkali atoms on the belt to reduce the ionization potential.

2 Claims, 3 Drawing Figures

IONIZATION OF ORGANIC SUBSTANCES ON CONVEYOR MEANS IN MASS SPECTROMETER

This application is a continuation-in-part of Ser. No. 855,579, filed Nov. 29, 1977, now U.S. Pat. No. 4,178,507.

BACKGROUND OF THE INVENTION

This invention relates to a process for the ionization of samples of organic substances transported by a conveyor belt from a liquid chromatograph (LC) into the vacuum area of a mass spectrometer (MS).

The coupling or combination of mass spectrometers with other analyzing devices has been known. The combination of a mass spectrometer with a liquid chromatograph is particularly advantageous since as a result, the good separating effect of the liquid chromatograph coincides with the good specificity of substance of the mass spectrometer.

While in a known coupling of a gas chromatograph with a mass spectrometer a separation of the substances is carried out in the gaseous state, and therefore the good volatility of such substances is a prerequisite, the LC/MS coupling will also permit the analysis of difficult to vaporize substances. The prerequisite, however, is that these substances may be dissolved and ionized in the mass spectrometer. In particular, many bio-chemically and medically important compounds belong to groups of these difficult to vaporize substances.

The consecutive connection of an LC and an MS has already been proposed. In the construction of such a combination one may, for example, proceed in such a way that the organic substance contained in a solvent is applied along with the solvent to a conveyor belt or wire which feeds the sample to a connected mass spectrometer. The conveyor belt leads up into the vacuum area of the mass spectrometer. This vacuum area is limited against the infeed area of the sample by underpressure sluices and suitable gaskets or packings. Prior to the entry of the sample into the vacuum area of the mass spectrometer the solvent is evaporated so that the dried sample on the belt is conveyed into the mass spectrometer.

The ionization of the organic sample reaching the mass spectrometer in this way constitutes a special problem. In this connection only electron impact ionization is known, which assumes that the sample evaporates in the vacuum area and is then ionized by electronic impact. The conveyor belt is properly heated for the evaporation of the sample.

Electronic impact ionization is particularly unfavorable or unsuitable in the investigation of sensitive organic substances. The molecule that is to be ionized absorbs internal energy twice in the case of this ionization process. Even during evaporation by heating, enough inner energy is absorbed so that a complete decomposition may occur in particularly sensitive substances. The additionally fed-in energy (beyond the ionization energy) during the electronic impact-ionization causes a further strong fragmentation of the molecules so that the mass spectra produced are no longer characteristic of the starting substance. For this reason, the LC/MS coupling combined with a conveyor belt has not yet gained acceptance in practice corresponding to the potential importance of such combination.

SUMMARY OF THE INVENTION

The invention is based on a process for the ionization of sensitive organic samples which are fed to an MS on a conveyor belt or a transportation wire coming from an LC in such a way that the mass spectrometric destruction or impairment of the molecules to be ionized is avoided. The process of the invention is characterized in that the sample is ionized directly on the conveyor belt or transportation wire by particle bombardment, and the ions are removed from it. In accordance with the invention, the sample may be acted upon on the conveyor belt in a concentrated manner with ions, electrons or photons, the latter with the use of a laser. The primary inventive concept common to the various embodiments requires the exposure of the sample on the conveyor belt always within a very short intervals, namely within fractions of seconds, to highly concentrated energy in such a way that by the concentration of energy, the molecule connections between molecules in the sample are locally separated without or prior to any chemical decomposition of the molecules. The advantage of this technique lies in the very careful treatment of the sample. Prior to chemical destruction, the molecule connections are separated by the local concentration of energy and ions are largely freed. The freed ions may then be fed in the customary manner to a mass spectrometer.

This process employs a conveyor belt or wire for transporting the sample. As a result of the effectively continuous, uniform movement thereby produced, the concentrated energy strikes a continuously changing area of the belt and thus of the sample. Only in this way does a sufficient yield of ions result without destruction of the sample In the case of use of a laser, a laser tube is disposed outside the vacuum area of the ionization chamber separated by a window which also acts as a lens. A 50 watt-$CO_2$ laser is suitable. The ionization on the surface of the conveyor belt may also take place by bombardment of the sample with electrons or ions.

Another possibility is to carry out the ionization by interaction of slow ions (at thermal speed) with the molecules of the sample on the surface of the conveyor belt. The ions, for example $CH_5+$ from methane, required for the ionization of the sample are produced in this case preferably in a plasma at elevated pressure, about 1 mbar. An elevated temperature of about 200°C. is provided in the ionization area.

The conveying means provided according to the invention, such as conveyor belt or conveyor wire, preferably are metal.

Various embodiments of the invention will be explained subsequently in more detail in conjunction with the drawings. These represent in rough schematization and simplification the coupling area between LC and an MS.

DETAILED DESCRIPTION OF THE PREFERRED EMBODIMENTS

Figure 1:
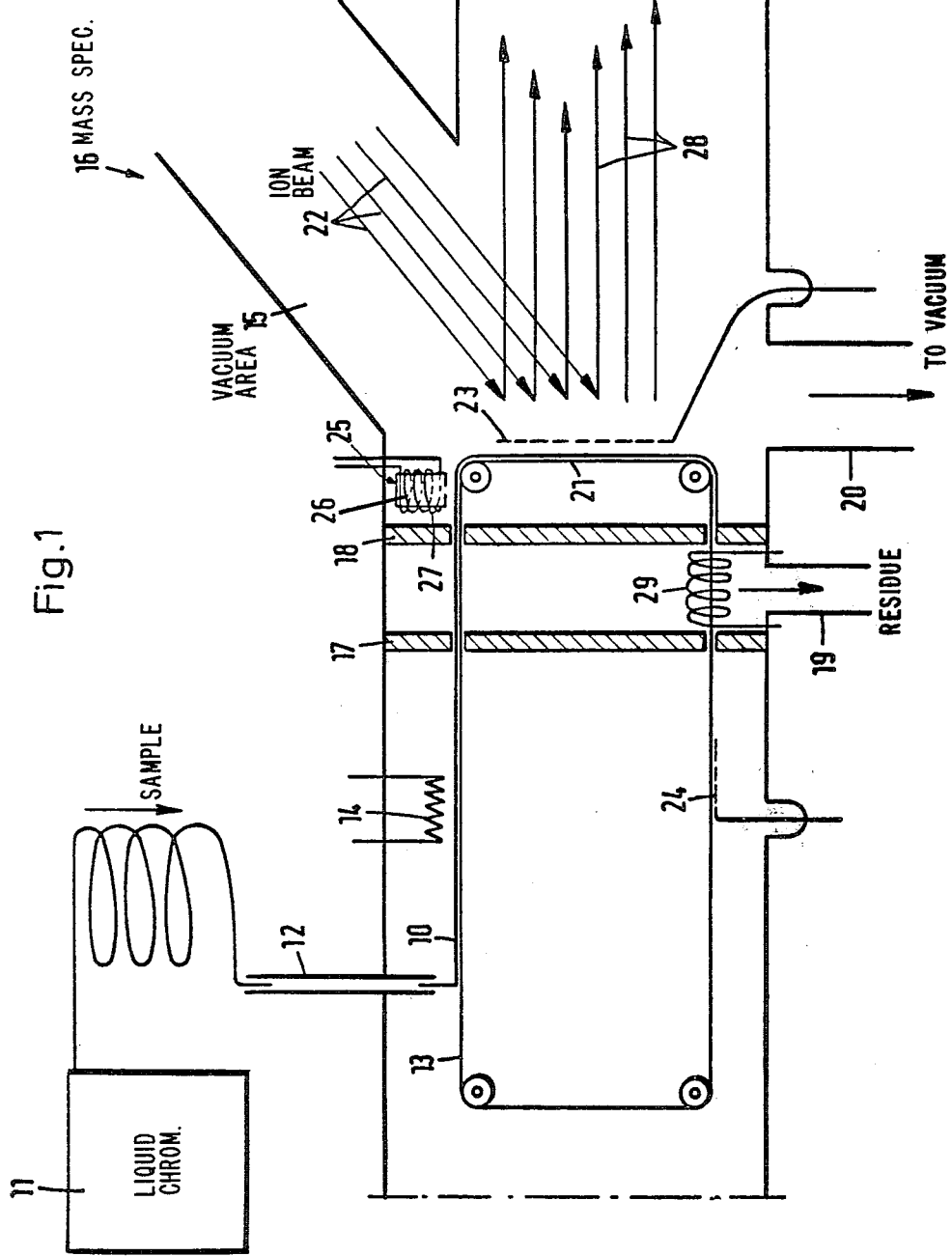
FIG. 1 shows a schematic embodiment of the invention featuring ionization by ion bombardment.

Referring now to the drawings, an organic sample 10, contained in a solvent, is applied by a liquid chromatograph 11 through a pipe 12 for the samples to an endless conveyor belt 13 or a transportation wire. The latter is preferably driven continuously in a clockwise direction.

The solvent is evaporated from the conveyor belt 13 by a heater 14. The dried sample 10 is then carried by the conveyor belt 13 into a vacuum area 15 (FIG. 1) of a mass spectrometer 16. The entry of the conveyor belt 13 into this vacuum area 15 as well as its exit from this area is protected against any loss of vacuum by two gaskets or packings 17 and 18. The area between the gaskets 17, 18 may be evacuated by a connection 19 to a first vacuum pump (not shown). A second vacuum pump is coupled by a connection 20 to the mass spectrometer 16.

The sample 10 is ionized directly on the conveyor belt 13 in the vacuum area 15 of the mass spectrometer 16. The ions are then removed from the conveyor belt 13 and are fed in the customary manner to an analyzer. This connected part of the mass spectrometer 16, not shown, may have any conventional form.

The ionization of the sample 10 on the conveyor belt 13 may take place in different ways. In the embodiment of FIG. 1, ionization by ion bombardment is shown schematically, whereby ion beams 22 with kinetic energies of a few keV are directed at the sample 10. As an alternative, ion bombardment may also take place with heavy ions of high energy (for example, many MeV). In both cases secondary ions 28 are produced which are accelerated in the customary manner and fed to the analyzer of the mass spectrometer 16.

In order to facilitate the separation of the ions from the surface of the conveyor belt 13 or of a conveyor wire, the image force between ions and mirror (image) charge may be neutralized by a strong, external electric field.

In the area of the vertical or erect part 21 of the conveyor belt 13 a thin screen 23 is disposed at a slight distance from the surface of the conveyor belt. This screen 23, consisting for example of gold or platinum, is supplied with a voltage to produce an electric field of, for example, about $10^4$ V/cm. The distance of the screen 23 from the belt surface is about 1 to 2 mm.

The conveyor belt 13 is subjected to a special treatment by which the work function is increased. Thus, a thin oxide layer is applied as a surface contaminant to the conveyor belt. In the present embodiment, a cathode 24 is disposed adjacent the conveyor belt outside of the vacuum area 15 and prior to the sample application. This cathode 24 causes the application of an oxide layer by glow discharge (anodic oxidation). Since the conveyor belt 13, after leaving the vacuum area 15, is always newly treated in this manner, the effect achieved of increasing the work function is continuously maintained. The oxide layer may be formed of the material of the conveyor belt 13, but may also be formed of a foreign material.

A further improvement of the ionization effect is brought about by lowering the ionization potential in a treatment zone of the conveyor belt 13 between the gaskets and after application of the sample 10. For this purpose, evaporation means 25 have been provided, which may comprise an oven 26 and a heater 27 which serves to vaporize alkali atoms. As a result, additional complexes from alkali atoms with organic energy will develop. For example, potassium, sodium, cesium, lithium, etc., are suitable for this purpose.

A heater 29 is also installed between the gaskets 17 and 18, by which a residue on the conveyor belt 13 or transportation wire is removed after the ionization process.

Figure 2:
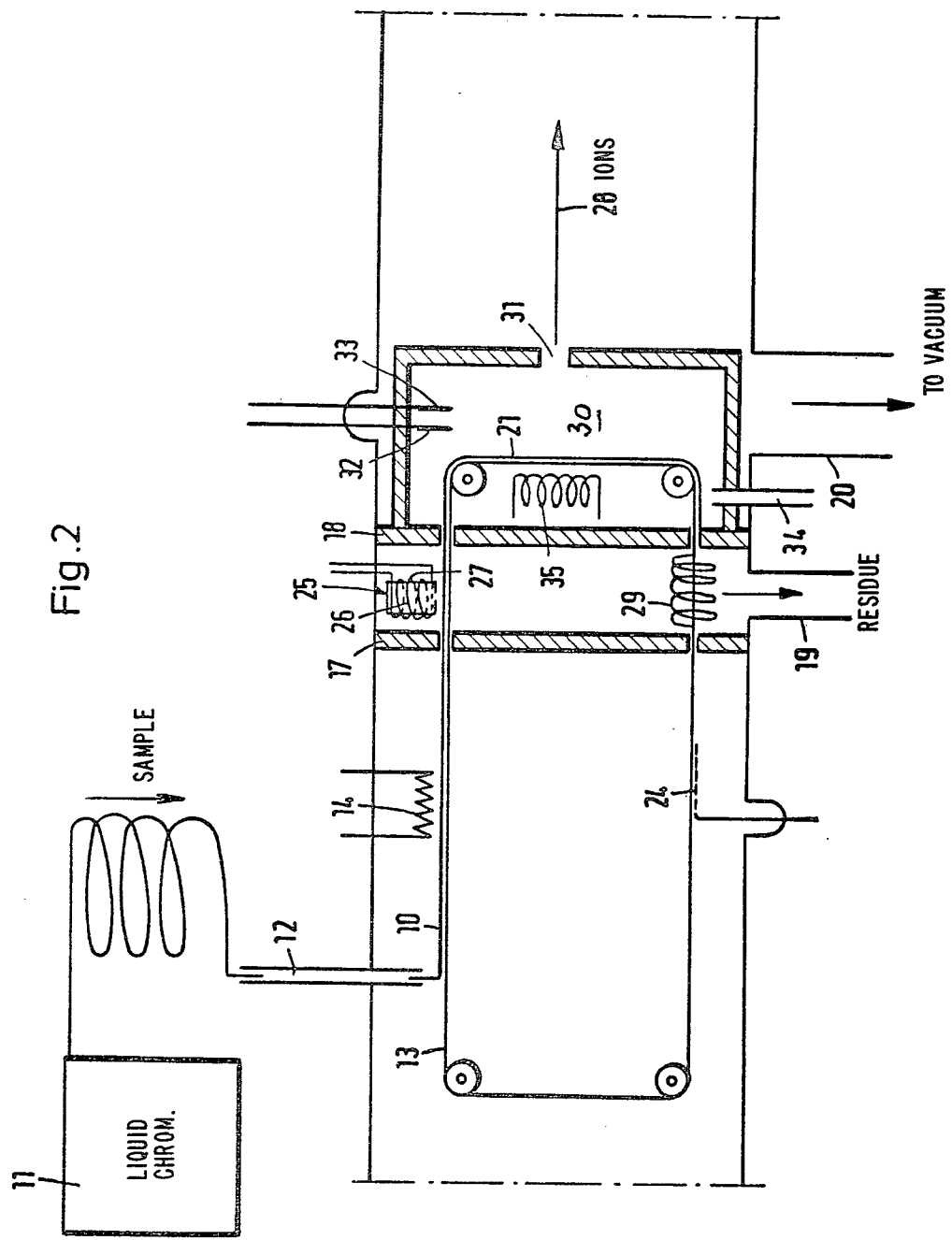
FIG. 2 shows a diagram similar to FIG. 1, but featuring ionization by gaseous charge carriers.

In the embodiment of FIG. 2, a special, smaller ionization space 30 is formed by homologous walls. The conveyor belt 13 with the applied sample 10 passes through this ionization space 30, and the otherwise sealed space has an exit aperture 31 for the ions.

Two electrodes 32 and 33 project into the ionization space 30, and a voltage of about 2 kV is applied across them. An inlet tube 34 is provided for a gas which serves as a charge carrier inside of the ionization space. A heater 35 is also installed within the ionization space 30 to produce a temperature of about 200° C., which is required for ionizing the sample 10 on the conveyor belt 13.

According to this alternative embodiment, ionization takes place as a result of the direct interaction of the sample 10 with the charge carrier under a thermal influence. The gas, such as methane, is ionized by the electrodes 32, 33 to about 1 KeV. The production of the charge carriers may also be performed by electrons emitted by a cathode instead of the electric discharge between electrodes 32, 33. The production of the charge carriers may also take place, instead of by an electric discharge between the electrodes 32, 33, for example by electrons which are emitted by a cathode. In order to achieve a high yield of ionization, a pressure of for example 1 torr is maintained in the ionization chamber 30.

Figure 3:
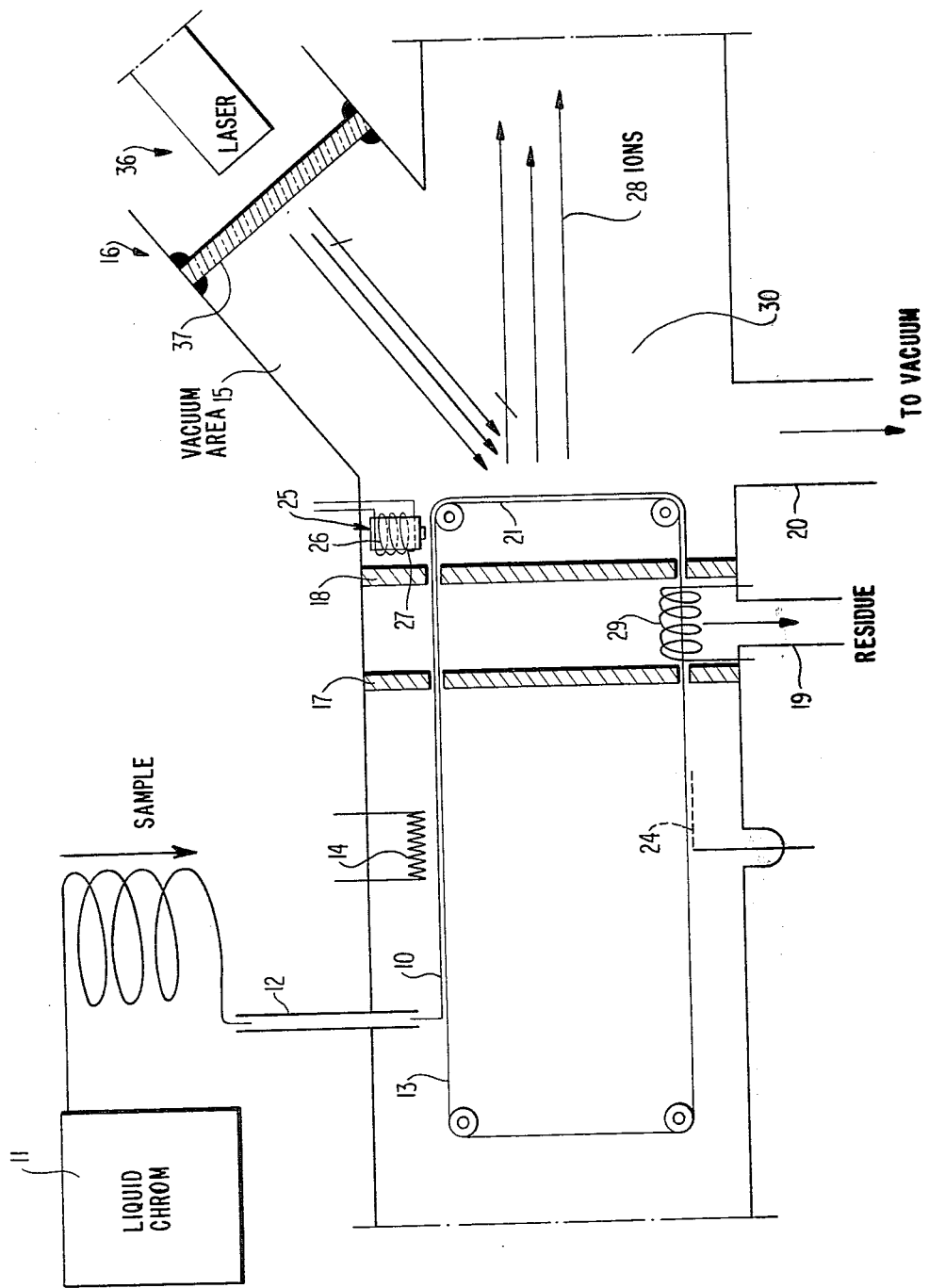
FIG. 3 is similar to FIGS. 1 and 2, but featuring laser ionization.

Ionization with a laser 36, for example a 50 watt-CO, is particularly advantageous. The latter is disposed outside the ionization chamber 30 or outside the vacuum area 15 and is separated by a window 37 made of glass or similar material. Effectively, the window 37 may be constructed as a focusing lens in order to provide an additional concentration of the laser beams. As a result, the laser beam is directed in a concentrated manner onto the upright stand 21 of the conveyor belt 13 or onto the sample 10 located thereon, so that ions 28 emerge which are fed in the customary manner to the mass spectrometer, not shown in detail. Otherwise, the embodiment of FIG. 3 operates in the same manner as that of FIG. 1.

What is claimed is:

1. A method for analyzing samples of substances in a solution obtained by a liquid chromatograph in a mass spectrometer comprising the steps of:
    transferring a sample of substance to be analyzed in a solution medium from a light chromatograph onto a moving continuous transport belt;
    vaporizing the solution medium to leave the substance on the belt;
    moving the belt so as to move the substance into a vacuum environment of an ionization chamber associated with said mass spectrometer;
    ionizing the sample directly on the moving belt in the ionization chamber by laser bombardment; and
    removing the ions from the belt and conducting them into the mass spectrometer.

2. The method of claim 1 wherein a laser tube for said laser bombardment is disposed outside of said vacuum environment in said ionization chamber, and an optical lens is provided in the wall of said chamber for concentrating a beam produced by said laser tube onto said sample.

* * * * *